(12) United States Patent
Nguyen et al.

(10) Patent No.: US 11,001,650 B2
(45) Date of Patent: May 11, 2021

(54) ELECTRON DONOR FOR POLYOLEFIN POLYMERIZATION CATALYSTS AND USES THEREOF

(71) Applicants: W.R. GRACE & CO.-CONN., Columbia, MD (US); BRASKEM AMERICA, INC., Philadelphia, PA (US)

(72) Inventors: Binh Thanh Nguyen, League City, TX (US); Jonas Alves Fernandes, Triunfo-RS (BR)

(73) Assignee: BRASKEM AMERICA, INC., Philadelphia, PA (US)

( * ) Notice: Subject to any disclaimer, the term of this patent is extended or adjusted under 35 U.S.C. 154(b) by 202 days.

(21) Appl. No.: 15/751,121

(22) PCT Filed: Aug. 11, 2016

(86) PCT No.: PCT/US2016/046560
§ 371 (c)(1),
(2) Date: Feb. 7, 2018

(87) PCT Pub. No.: WO2017/027710
PCT Pub. Date: Feb. 16, 2017

(65) Prior Publication Data
US 2018/0230252 A1    Aug. 16, 2018

Related U.S. Application Data

(60) Provisional application No. 62/203,821, filed on Aug. 11, 2015.

(51) Int. Cl.
| | | |
|---|---|---|
| *C08F 10/06* | (2006.01) | |
| *C07C 43/164* | (2006.01) | |
| *C07C 49/788* | (2006.01) | |
| *C07C 63/46* | (2006.01) | |
| *B01J 31/12* | (2006.01) | |
| *C08F 110/06* | (2006.01) | |
| *B01J 31/02* | (2006.01) | |

(52) U.S. Cl.
CPC .............. *C08F 10/06* (2013.01); *B01J 31/02* (2013.01); *B01J 31/12* (2013.01); *C07C 43/164* (2013.01); *C07C 49/788* (2013.01); *C07C 63/46* (2013.01); *C08F 110/06* (2013.01)

(58) Field of Classification Search
CPC ..... C08F 10/06; C07C 43/164; C07C 49/788; C07C 63/46
See application file for complete search history.

(56) References Cited

U.S. PATENT DOCUMENTS

| | | |
|---|---|---|
| 2008/0027189 A1 | 1/2008 | Marin et al. |
| 2013/0109789 A1 | 5/2013 | Hamaki et al. |
| 2015/0268567 A1* | 9/2015 | Iwasaki ................ G03G 5/0517 430/56 |

FOREIGN PATENT DOCUMENTS

| | | | | |
|---|---|---|---|---|
| CN | 104211930 A | 12/2014 | | |
| EP | 0605380 A2 | * 7/1994 | ............ | C08F 4/6065 |
| EP | 2 803 678 A1 | 11/2014 | | |
| JP | S49-088851 A | 8/1974 | | |
| JP | S56-010130 A | 2/1981 | | |
| JP | H02215809 | * 8/1990 | | |
| JP | 2008-521243 A | 6/2008 | | |
| JP | 2010-150440 A | 7/2010 | | |
| JP | 2013-028704 A | 2/2013 | | |
| JP | 2013028704 A | * 2/2013 | | |
| WO | WO-03/068828 A1 | 8/2003 | | |
| WO | WO-2009/152211 A2 | 12/2009 | | |

OTHER PUBLICATIONS

Translation of JP 2013-028704A. (Year: 2013).*
Zhang et al., "Control of molecular weight distribution for polypropylene obtained by commercial Ziegler-Natta catalyst: effect of temperature," Polym. Bull. (2011) 67:1519-1527. (Year: 2011).*
Extended European Search Report in EP Application No. 16835914.9, dated Mar. 15, 2019 (11 pages).
Melvin S. Newman et al: "Synthesis of 6,6'-diethynyldiphenic anhydride," Journal of Organic Chemistry, vol. 36, No. 10, May 1, 1971, pp. 1398-1401.
R. Munday et al: "The study of conformational changes in 4,5-disubstituted phenanthrenes by nuclear magnetic resonance spectroscopy," Journal of the Chemical Society, Section B: Physical Organic Chemistry, Jan. 1, 1968, pp. 80-84.
Shin-Ichi Kondo et al: "Cooperativity of binuclear Zn(II) complexes of bisimidazolyl ligands in the hydrolysis of bis(2,4-dinitrophenyl) phosphate in aqueous solution," Journal of the Chemical Society, Perkin Transactions 2., No. 1, Dec. 18, 2000, pp. 128-131.
International Search Report & Written Opinion in International Application No. PCT/US2016/046560, dated Dec. 30, 2016 (9 pages).
PUBCHEM, Substance Record for SID 104504818. Create Date: Feb. 18, 2011. [retrieved on Feb. 7, 2018]. Retrieved from the Internet: https://pubchem.ncbi.nlm.nih.gov/substance/104504818.
PUBCHEM, Substance Record for SID 125657412. Create Date: Oct. 30, 2011. [retrieved on Feb. 7, 2018]. Retrieved from the Internet: https://pubchem.ncbi.nlm.nih.gov/substance/125657412.
Bowden, K., et al., "Reactions of carbonyl compounds in basic solutions. Part 26. The mechanisms of the base-catalyzed cyclisation of 1,2-diacetylbenzene, 1,8-diacetylnaphthalene, 4,5-diacetylphenanthrene and 2,2'-diacetylbiphenyl," J. Chem. Soc., Perkin Trans., 2(5):997-1001 (1997).
Gu, S., et al., "Di-n-propyl anthracene-1,8dicarbosylate," Acta Cryst., Structure Reports Online, E62:o5001-o5002 (2006).

(Continued)

*Primary Examiner* — Catherine S Branch

(74) *Attorney, Agent, or Firm* — Foley & Lardner LLP

(57) ABSTRACT

Disclosed in certain embodiments is an electron donor for a polyolefin polymerization catalyst. In some embodiments, a solid catalyst component includes a metal component and the electron donor that form a catalyst on a support.

10 Claims, No Drawings

(56) References Cited

OTHER PUBLICATIONS

Hiramatsu, T., et al., "Studies on Chemiluminescent Compounds. I. Synthesis of Acyl-substituted Anthracene Derivatives and Their Chemiluminescence," Chem. Soc. Jpn., Bull. Chem. Soc. Jpn., 54:985-990 (1981).
Science of Synthesis, vol. 45b, pp. 816-817 (2010).
Table 28: Biphenylenes Via Intermolecular Coupling, Org. Reactions, 451-452 (2004).
Tang, R., et al., "Efficient Approach to Electron-Deficient 1,2,7,8-Tetraazaperylene Derivatives," Org. Lett., 16:4726-4729 (2014).
Wilcox, C., et al., "Synthesis and Properties of Cycloocta[def]biphenylene-1,4-dione," J. Org. Chem., 54(9):2190-2197 (1989).
Zhang, H., et al., "Diisopropyl anthracene-1,8-dicarboxylate," Acta Cryst., Structure Reports Online, E63:o175-o176 (2007).

* cited by examiner

ELECTRON DONOR FOR POLYOLEFIN POLYMERIZATION CATALYSTS AND USES THEREOF

CROSS REFERENCE TO RELATED APPLICATIONS

This application is a U.S. National Phase Application under 35 U.S.C. § 371 of International Application No. PCT/US2016/046560, filed on Aug. 11, 2016, which claims the benefit of priority of U.S. Provisional Patent Application Ser. No. 62/203,821, filed Aug. 11, 2015, the disclosures of which are hereby incorporated by reference herein in their entireties.

FIELD OF THE INVENTION

The present invention relates to catalysts for polymerization and, more specifically, to electron donors used in polyolefin polymerization catalysts.

BACKGROUND

The performance of catalysts used in polyolefin polymerization is typically evaluated in terms of xylene solubles content, melt flow, and polydispersity of the resulting polymer. Traditional catalysts, however, often result in high xylene solubles content of the resulting polymer, and it is difficult to dynamically adjust the xylene solubility during the production process with such catalysts. Moreover, such catalysts suffer from low hydrogen response (i.e., chain termination in response to introduction of hydrogen during the reaction), which limits the ability to adjust physical parameters of the resulting polymer, such as melt flow.

OBJECTS AND SUMMARY OF THE INVENTION

It is an object of certain embodiments of the present invention to provide an electron donor for use in a polyolefin polymerization catalyst.

It is an object of certain embodiments of the present invention to provide a catalyst that is phthalate free.

It is an object of certain embodiments of the present invention to provide a catalyst with high catalytic activity.

It is an object of certain embodiments of the present invention to provide a method of producing polymer having improved properties.

It is an object of certain embodiments of the present invention to provide a catalyst with improved hydrogen response.

It is an object of certain embodiments of the present invention to provide a catalyst for producing polymer with low xylene solubility (i.e., low xylene solubles content).

One or more of the above objects and others are met by the present invention, in which certain embodiments are directed to a compound of Formula I:

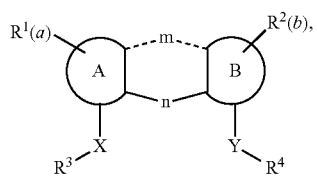

wherein the variables are as disclosed herein.

In certain embodiments, the present invention is directed to a compound of Formula I.a:

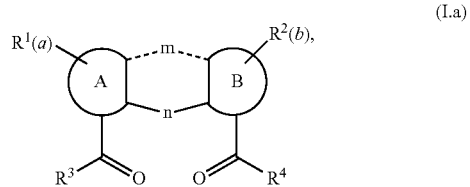

wherein the variables are as disclosed herein.

In certain embodiments, the present invention is directed to a compound of Formula I.b:

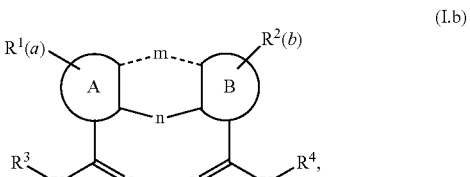

wherein the variables are as disclosed herein.

One or more of the above objects and others are met by the present invention, in which certain embodiments are directed to a compound of Formula I:

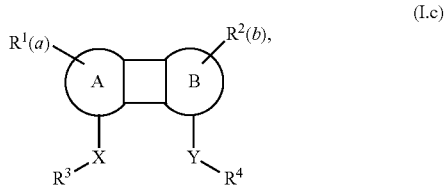

wherein the variables are as disclosed herein.

One or more of the above objects and others are met by the present invention, in which certain embodiments are directed to a compound of Formula I:

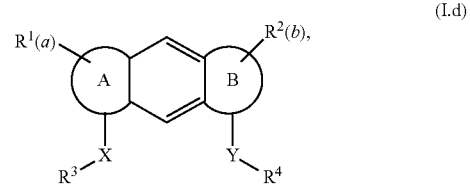

wherein the variables are as disclosed herein.

One or more of the above objects and others are met by the present invention, in which certain embodiments are directed to a compound of Formula I:

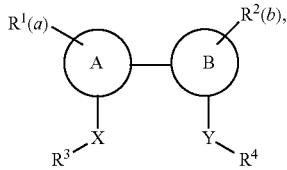

(I.e)

wherein the variables are as disclosed herein.

In certain embodiments, the present invention is directed to a compound of Formula II:

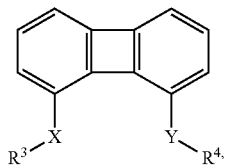

(II)

In certain embodiments, the present invention is directed to a compound of Formula III:

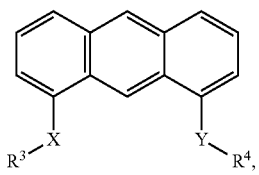

(III)

wherein the variables are as disclosed herein.

In certain embodiments, the present invention is directed to a compound of Formula IV:

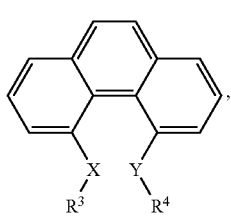

(IV)

wherein the variables are as disclosed herein.

Certain other embodiments of the present invention are directed to a compound of Formula V:

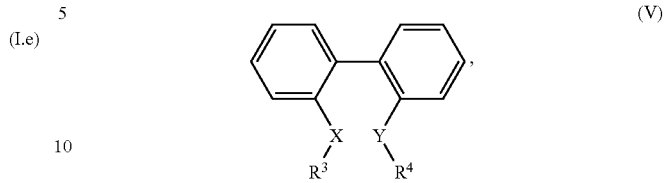

(V)

wherein the variables are as disclosed herein.

In certain embodiments, the present invention is directed to a catalyst system for use in olefinic polymerization, the catalyst system including a compound of Formula I, II, III, IV, or V, an organoaluminum compound, and, optionally, an organosilicon compound. In certain embodiments, the organosilicon compound is added during the polymerization process as an external electron donor. In other embodiments, the organosilicon compound is part of the catalyst as an internal electron donor.

In certain embodiments, the present invention is directed to a method of producing a polyolefin catalyst, the method including forming a reaction mixture of a support and a titanium salt, and adding an electron donor having the composition of Formula I, II, III, IV, or V.

In certain embodiments, the present invention is directed to a method of producing polypropylene, the method including forming a reaction mixture by mixing a silane component with a catalyst component, with the catalyst component including a titanium catalyst and an electron donor (e.g., a compound having the composition of Formula I, II, III, IV, or V. The method further includes adding propylene to the reaction mixture to form a polypropylene batch. In certain embodiments, the electron donor is a non-phthalate electron donor.

For the purpose of the present disclosure, the term "alkyl" as used by itself or as part of another group refers to a linear or branched chain aliphatic hydrocarbon containing one to twelve carbon atoms (i.e., $C_{1-12}$ alkyl) or the number of carbon atoms designated (i.e., a $C_1$ alkyl such as methyl, a $C_2$ alkyl such as ethyl, a $C_3$ alkyl such as propyl or isopropyl, etc.). In one embodiment, the alkyl group is chosen from a linear chain $C_{1-10}$ alkyl group. In another embodiment, the alkyl group is chosen from a branched chain $C_{1-10}$ alkyl group. In another embodiment, the alkyl group is chosen from a linear chain $C_{1-6}$ alkyl group. In another embodiment, the alkyl group is chosen from a branched chain $C_{1-6}$ alkyl group. In another embodiment, the alkyl group is chosen from a linear chain $C_{1-4}$ alkyl group. In another embodiment, the alkyl group is chosen from a branched chain $C_{1-4}$ alkyl group. In another embodiment, the alkyl group is chosen from a linear or branched chain $C_{2-4}$ alkyl group. Non-limiting exemplary $C_{1-10}$ alkyl groups include methyl, ethyl, propyl, isopropyl, butyl, sec-butyl, tert-butyl, iso-butyl, 3-pentyl, hexyl, heptyl, octyl, nonyl, decyl, and the like. Non-limiting exemplary $C_{1-4}$ alkyl groups include methyl, ethyl, propyl, isopropyl, butyl, sec-butyl, tert-butyl, and iso-butyl.

For the purpose of the present disclosure, the term "optionally substituted alkyl" as used by itself or as part of another group means that the alkyl as defined above is either unsubstituted or substituted with one, two, or three substituents independently chosen from nitro, haloalkoxy, aryloxy, aralkyloxy, alkylthio, sulfonamido, alkylcarbonyl, arylcarbonyl, alkylsulfonyl, arylsulfonyl, ureido, guanidino, carboxy, carboxyalkyl, cycloalkyl, and the like. In one embodiment, the optionally substituted alkyl is substituted with two substituents. In another embodiment, the optionally substituted alkyl is substituted with one substituent. Non-limiting exemplary optionally substituted alkyl groups include —CH$_2$CH$_2$NO$_2$, —CH$_2$CH$_2$CO$_2$H, —CH$_2$CH$_2$SO$_2$CH$_3$, —CH$_2$CH$_2$COPh, —CH$_2$C$_6$H$_{11}$, and the like.

For the purpose of the present disclosure, the term "cycloalkyl" as used by itself or as part of another group refers to saturated and partially unsaturated (containing one or two double bonds) cyclic aliphatic hydrocarbons containing one to three rings having from three to twelve carbon atoms (i.e., C$_{3-12}$ cycloalkyl) or the number of carbons designated. In one embodiment, the cycloalkyl group has two rings. In one embodiment, the cycloalkyl group has one ring. In another embodiment, the cycloalkyl group is chosen from a C$_{3-8}$ cycloalkyl group. In another embodiment, the cycloalkyl group is chosen from a C$_{3-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, and the like.

For the purpose of the present disclosure, the term "optionally substituted cycloalkyl" as used by itself or as part of another group means that the cycloalkyl as defined above is either unsubstituted or substituted with one, two, or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted cycloalkyl is substituted with two substituents. In another embodiment, the optionally substituted cycloalkyl is substituted with one substituent. Non-limiting exemplary optionally substituted cycloalkyl groups include:

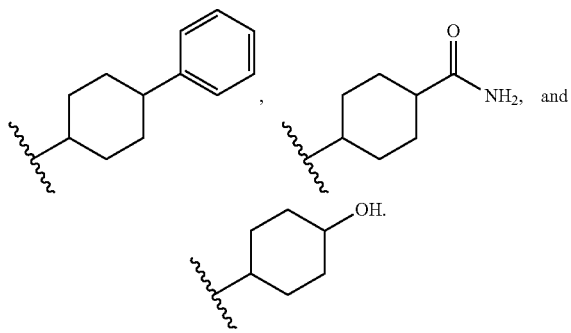

For the purpose of the present disclosure, the term "cycloalkenyl" as used by itself or part of another group refers to a partially unsaturated cycloalkyl group as defined above. In one embodiment, the cycloalkenyl has one carbon-to-carbon double bond. In another embodiment, the cycloalkenyl group is chosen from a C$_{4-8}$ cycloalkenyl group. Exemplary cycloalkenyl groups include cyclopentenyl, cyclohexenyl, and the like.

For the purpose of the present disclosure, the term "optionally substituted cycloalkenyl" as used by itself or as part of another group means that the cycloalkenyl as defined above is either unsubstituted or substituted with one, two, or three substituents independently chosen from halo, nitro, cyano, hydroxy, amino, alkylamino, dialkylamino, haloalkyl, monohydroxyalkyl, dihydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted cycloalkenyl is substituted with two substituents. In another embodiment, the optionally substituted cycloalkenyl is substituted with one substituent. In another embodiment, the cycloalkenyl is unsubstituted.

For the purpose of the present disclosure, the term "alkenyl" as used by itself or as part of another group refers to an alkyl group as defined above containing one, two or three carbon-to-carbon double bonds. In one embodiment, the alkenyl group is chosen from a C$_{2-6}$ alkenyl group. In another embodiment, the alkenyl group is chosen from a C$_{2-4}$ alkenyl group. Non-limiting exemplary alkenyl groups include ethenyl, propenyl, isopropenyl, butenyl, sec-butenyl, pentenyl, and hexenyl.

For the purpose of the present disclosure, the term "optionally substituted alkenyl" as used herein by itself or as part of another group means the alkenyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, or heterocyclo.

For the purpose of the present disclosure, the term "alkynyl" as used by itself or as part of another group refers to an alkyl group as defined above containing one to three carbon-to-carbon triple bonds. In one embodiment, the alkynyl has one carbon-to-carbon triple bond. In one embodiment, the alkynyl group is chosen from a C$_{2-6}$ alkynyl group. In another embodiment, the alkynyl group is chosen from a C$_{2-4}$ alkynyl group. Non-limiting exemplary alkynyl groups include ethynyl, propynyl, butynyl, 2-butynyl, pentynyl, and hexynyl groups.

For the purpose of the present disclosure, the term "optionally substituted alkynyl" as used herein by itself or as part of another group means the alkynyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, or heterocyclo.

For the purpose of the present disclosure, the term "haloalkyl" as used by itself or as part of another group refers to an alkyl group substituted by one or more fluorine, chlorine, bromine and/or iodine atoms. In one embodiment, the alkyl group is substituted by one, two, or three fluorine and/or chlorine atoms. In another embodiment, the haloalkyl group is chosen from a C$_{1-4}$ haloalkyl group. Non-limiting exemplary haloalkyl groups include fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

For the purpose of the present disclosure, the term "hydroxyalkyl" as used by itself or as part of another group refers to an alkyl group substituted with one or more, e.g., one, two, or three, hydroxy groups. In one embodiment, the hydroxyalkyl group is a monohydroxyalkyl group, i.e., substituted with one hydroxy group. In another embodiment, the hydroxyalkyl group is a dihydroxyalkyl group, i.e., substituted with two hydroxy groups. In another embodiment, the hydroxyalkyl group is chosen from a $C_{1-4}$ hydroxyalkyl group. Non-limiting exemplary hydroxyalkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

For the purpose of the present disclosure, the term "alkoxy" as used by itself or as part of another group refers to an optionally substituted alkyl, optionally substituted cycloalkyl, optionally substituted alkenyl, optionally substituted cycloalkenyl, optionally substituted alkynyl or optionally substituted alkynyl attached to a terminal oxygen atom. In one embodiment, the alkoxy group is chosen from a $C_{1-4}$ alkoxy group. In another embodiment, the alkoxy group is chosen from a $C_{1-4}$ alkyl attached to a terminal oxygen atom, e.g., methoxy, ethoxy, and tert-butoxy.

For the purpose of the present disclosure, the term "alkoxyalkyl" as used by itself or as part of another group refers to an alkyl group substituted with an alkoxy group. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

For the purpose of the present disclosure, the term "heteroalkyl" as used by itself or part of another group refers to a stable linear or branched chain hydrocarbon radical containing 1 to 10 carbon atoms and at least two heteroatoms, which can be the same or different, selected from O, N, or S, wherein: 1) the nitrogen atom(s) and sulfur atom(s) can optionally be oxidized; and/or 2) the nitrogen atom(s) can optionally be quaternized. The heteroatoms can be placed at any interior position of the heteroalkyl group or at a position at which the heteroalkyl group is attached to the remainder of the molecule. In one embodiment, the heteroalkyl group contains two oxygen atoms. Non-limiting exemplary heteroalkyl groups include —$CH_2OCH_2CH_2OCH_3$, —$OCH_2CH_2OCH_2CH_2OCH_3$, —$CH_2NHCH_2CH_2OCH_2$, —$OCH_2CH_2NH_2$, and —$NHCH_2CH_2N(H)CH_3$.

For the purpose of the present disclosure, the term "haloalkoxy" as used by itself or as part of another group refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

For the purpose of the present disclosure, the term "aryl" as used by itself or as part of another group refers to a monocyclic, bicyclic, or polycyclic aromatic ring system having from six to fourteen carbon atoms (i.e., $C_{6-14}$ aryl). Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is chosen from phenyl, naphthyl, anthracene, or phenanthrene.

For the purpose of the present disclosure, the term "optionally substituted aryl" as used herein by itself or as part of another group means that the aryl as defined above is either unsubstituted or substituted with one to five substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, or (heteroaryl)alkyl. In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, and 3-chloro-4-fluorophenyl. The term optionally substituted aryl is meant to include groups having fused optionally substituted cycloalkyl and fused optionally substituted heterocyclo rings. Examples include:

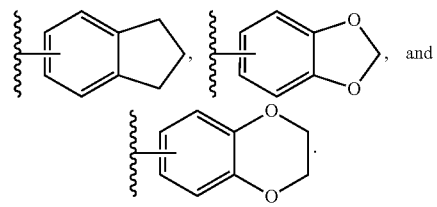

For the purpose of the present disclosure, the term "aryloxy" as used by itself or as part of another group refers to an optionally substituted aryl attached to a terminal oxygen atom. A non-limiting exemplary aryloxy group is PhO—.

For the purpose of the present disclosure, the term "aralkyloxy" as used by itself or as part of another group refers to an aralkyl group attached to a terminal oxygen atom. A non-limiting exemplary aralkyloxy group is $PhCH_2O$—.

For the purpose of the present disclosure, the term "heteroaryl" or "heteroaromatic" refers to monocyclic, bicyclic, and polycyclic aromatic ring systems having 5 to 14 ring atoms (i.e., $C_{5-14}$ heteroaryl) and 1, 2, 3, or 4 heteroatoms independently chosen from oxygen, nitrogen and sulfur. In one embodiment, the heteroaryl has three heteroatoms. In another embodiment, the heteroaryl has two heteroatoms. In another embodiment, the heteroaryl has one heteroatom. In one embodiment, the heteroaryl is a $C_5$ heteroaryl. In another embodiment, the heteroaryl is a $C_6$ heteroaryl. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, pyrimidin-5-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl). The term "heteroaryl" is also meant to include possible N-oxides. Exemplary N-oxides include pyridyl N-oxide, and the like.

For the purpose of the present disclosure, the term "optionally substituted heteroaryl" as used by itself or as part of another group means that the heteroaryl as defined above is either unsubstituted or substituted with one to four substituents, e.g., one or two substituents, independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted heteroaryl has one substituent. In one embodiment, the optionally substituted is an optionally substituted pyridyl, i.e., 2-, 3-, or 4-pyridyl. Any available carbon or nitrogen atom can be substituted. In another embodiment, the optionally substituted heteroaryl is an optionally substituted indole.

For the purpose of the present disclosure, the term "heterocycle" or "heterocyclo" as used by itself or as part of another group refers to saturated and partially unsaturated (e.g., containing one or two double bonds) cyclic groups containing one, two, or three rings having from three to fourteen ring members (i.e., a 3- to 14-membered heterocyclo) and at least one heteroatom. Each heteroatom is independently selected from the group consisting of oxygen, sulfur, including sulfoxide and sulfone, and/or nitrogen atoms, which can be quaternized. The term "heterocyclo" is meant to include cyclic ureido groups such as 2-imidazolidinone and cyclic amide groups such as β-lactam, γ-lactam, δ-lactam and ε-lactam. The term "heterocyclo" is also meant to include groups having fused optionally substituted aryl groups, e.g., indolinyl. In one embodiment, the heterocyclo group is chosen from a 5- or 6-membered cyclic group containing one ring and one or two oxygen and/or nitrogen atoms. The heterocyclo can be optionally linked to the rest of the molecule through a carbon or nitrogen atom. Non-limiting exemplary heterocyclo groups include 2-imidazolidinone, piperidinyl, morpholinyl, piperazinyl, pyrrolidinyl, and indolinyl.

For the purpose of the present disclosure, the term "optionally substituted heterocyclo" as used herein by itself or part of another group means the heterocyclo as defined above is either unsubstituted or substituted with one to four substituents independently selected from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (heteroaryl)alkyl, and the like. Substitution may occur on any available carbon or nitrogen atom, and may form a spirocycle. Non-limiting exemplary optionally substituted heterocyclo groups include:

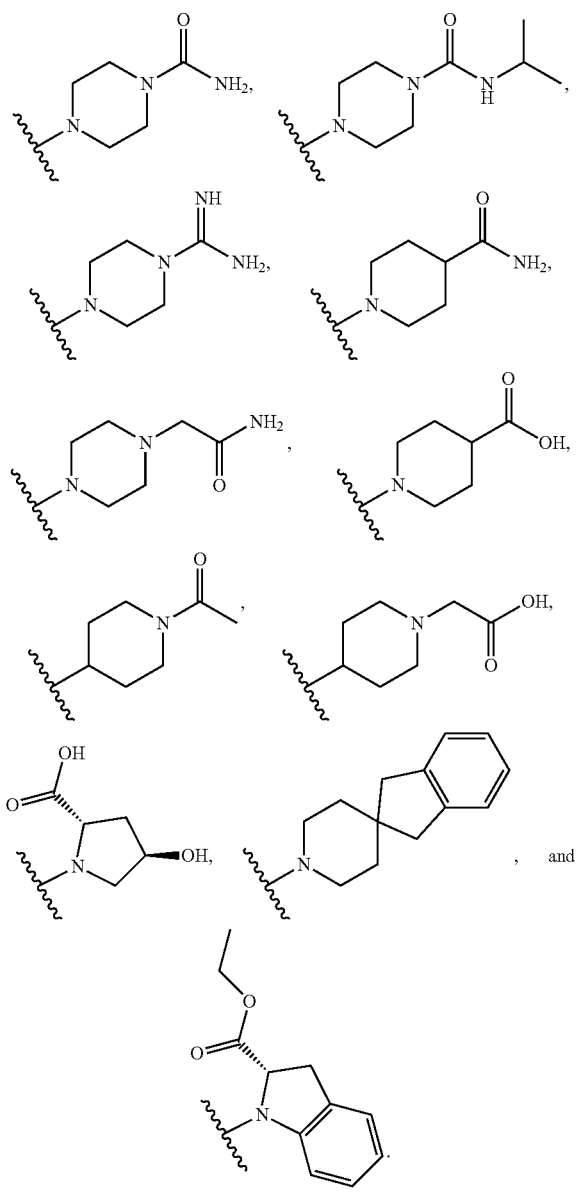

For the purpose of the present disclosure, the term "amino" as used by itself or as part of another group refers to —NH$_2$.

For the purpose of the present disclosure, the term "alkylamino" as used by itself or as part of another group refers to —NHR$^{15}$, wherein R$^{15}$ is alkyl.

For the purpose of the present disclosure, the term "dialkylamino" as used by itself or as part of another group refers to —NR$^{16a}$R$^{16b}$, wherein R$^{16a}$ and R$^{16b}$ are each independently alkyl or R$^{16a}$ and R$^{16b}$ are taken together to form a 3- to 8-membered optionally substituted heterocyclo.

For the purpose of the present disclosure, the term "hydroxyalkylamino" as used by itself or as part of another group refers to —NHR$^{17}$, wherein R$^{17}$ is hydroxyalkyl.

For the purpose of the present disclosure, the term "(amino)alkyl" as used by itself or as part of another group refers to an alkyl group substituted with an amino group. Non-limiting exemplary amino alkyl groups include —CH$_2$CH$_2$NH$_2$, —CH$_2$CH$_2$CH$_2$NH$_2$, —CH$_2$CH$_2$CH$_2$CH$_2$NH$_2$, and the like.

For the purpose of the present disclosure, the term "(alkylamino)alkyl" as used by itself or as part of another group refers alkyl group substituted an alkylamino group. A non-limiting exemplary (alkylamino)alkyl group is —CH$_2$CH$_2$N(H)CH$_3$.

For the purpose of the present disclosure, the term "(dialkylamino)alkyl" as used by itself or as part of another group refers to an alkyl group substituted by a dialkylamino group. A non-limiting exemplary (dialkylamino)alkyl group is —CH$_2$CH$_2$N(CH$_3$)$_2$.

For the purpose of the present disclosure, the term "(cyano)alkyl" as used by itself or as part of another group refers to an alkyl group substituted with one or more cyano, e.g., —CN, groups. Non-limiting exemplary (cyano)alkyl groups include —CH$_2$CH$_2$CN, —CH$_2$CH$_2$CH$_2$CN, and —CH$_2$CH$_2$CH$_2$CH$_2$CN.

For the purpose of the present disclosure, the term "carboxamido" as used by itself or as part of another group refers to a radical of formula —C(=O)NR$^{24a}$R$^{24b}$, wherein R$^{24a}$ and R$^{24b}$ are each independently hydrogen, optionally substituted alkyl, optionally substituted aryl, or optionally substituted heteroaryl, or R$^{24a}$ and R$^{24b}$ taken together with the nitrogen to which they are attached from a 3- to 8-membered heterocyclo group. In one embodiment, R$^{24a}$ and R$^{24b}$ are each independently hydrogen or optionally substituted alkyl. Non-limiting exemplary carboxamido groups include —CONH$_2$, —CON(H)CH$_3$, —CON(CH$_3$)$_2$, and —CON(H)Ph.

For the purpose of the present disclosure, the term "(carboxamido)alkyl" as used by itself or as part of another group refers to an alkyl group with a carboxamido group. Non-limiting exemplary (carboxamido)alkyl groups include —CH$_2$CONH$_2$, —C(H)CH$_3$—CONH$_2$, and —CH$_2$CON(H)CH$_3$.

For the purpose of the present disclosure, the term "sulfonamido" as used by itself or as part of another group refers to a radical of the formula —SO$_2$NR$^{23a}$R$^{23b}$, wherein R$^{23a}$ and R$^{23b}$ are each independently hydrogen, optionally substituted alkyl, or optionally substituted aryl, or R$^{23a}$ and R$^{23b}$ taken together with the nitrogen to which they are attached from a 3- to 8-membered heterocyclo group. Non-limiting exemplary sulfonamido groups include —SO$_2$NH$_2$, —SO$_2$N(H)CH$_3$, and —SO$_2$N(H)Ph.

For the purpose of the present disclosure, the term "alkylcarbonyl" as used by itself or as part of another group refers to a carbonyl group, i.e., —C(=O)—, substituted by an alkyl group. A non-limiting exemplary alkylcarbonyl group is —COCH$_3$.

For the purpose of the present disclosure, the term "arylcarbonyl" as used by itself or as part of another group refers to a carbonyl group, i.e., —C(=O)—, substituted by an optionally substituted aryl group. A non-limiting exemplary arylcarbonyl group is —COPh.

For the purpose of the present disclosure, the term "alkylsulfonyl" as used by itself or as part of another group refers to a sulfonyl group, i.e., —SO$_2$—, substituted by any of the above-mentioned optionally substituted alkyl groups. A non-limiting exemplary alkylsulfonyl group is —SO$_2$CH$_3$.

For the purpose of the present disclosure, the term "arylsulfonyl" as used by itself or as part of another group refers to a sulfonyl group, i.e., —SO$_2$—, substituted by any of the above-mentioned optionally substituted aryl groups. A non-limiting exemplary arylsulfonyl group is —SO$_2$Ph.

For the purpose of the present disclosure, the term "mercaptoalkyl" as used by itself or as part of another group refers to any of the above-mentioned alkyl groups substituted by a —SH group.

For the purpose of the present disclosure, the term "carboxy" as used by itself or as part of another group refers to a radical of the formula —COOH.

For the purpose of the present disclosure, the term "carboxyalkyl" as used by itself or as part of another group refers to any of the above-mentioned alkyl groups substituted with a —COOH. A non-limiting exemplary carboxyalkyl group is —CH$_2$CO$_2$H.

For the purpose of the present disclosure, the term "aralkyl" as used by itself or as part of another group refers to an alkyl group substituted with one, two, or three optionally substituted aryl groups. In one embodiment, the aralkyl group is a C$_{1-4}$ alkyl substituted with one optionally substituted aryl group. Non-limiting exemplary aralkyl groups include benzyl, phenethyl, —CHPh$_2$, and —CH(4-FPh)$_2$.

For the purpose of the present disclosure, the term "ureido" as used by itself or as part of another group refers to a radical of the formula —NR$^{22a}$C(=O)NR$^{22b}$R$^{22c}$, wherein R$^{22a}$ is hydrogen, alkyl, or optionally substituted aryl, and R$^{22b}$ and R$^{22c}$ are each independently hydrogen, alkyl, or optionally substituted aryl, or R$^{22b}$ and R$^{22c}$ taken together with the nitrogen to which they are attached form a 4- to 8-membered heterocyclo group. Non-limiting exemplary ureido groups include —NHC(=O)NH$_2$ and —NHC(=O)NHCH$_3$.

For the purpose of the present disclosure, the term "guanidino" as used by itself or as part of another group refers to a radical of the formula —NR$^{25a}$C(=NR$^{26}$)NR$^{25b}$R$^{25c}$, wherein R$^{25a}$, R$^{25b}$, and R$^{25c}$ are each independently hydrogen, alkyl, or optionally substituted aryl, and R$^{26}$ is hydrogen, alkyl, cyano, alkylsulfonyl, alkylcarbonyl, carboxamido, or sulfonamido. Non-limiting exemplary guanidino groups include —NHC(=NH)NH$_2$, —NHC(=NCN)NH$_2$, —NHC(=NH)NHCH$_3$, and the like.

For the purpose of the present disclosure, the term "(heterocyclo)alkyl" as used by itself or as part of another group refers to an alkyl group substituted with one, two, or three optionally substituted heterocyclo groups. In one embodiment, the (heterocyclo)alkyl is a (C$_{1-4}$)alkyl substituted with one optionally substituted heterocyclo group. Non-limiting exemplary (heterocyclo)alkyl groups include:

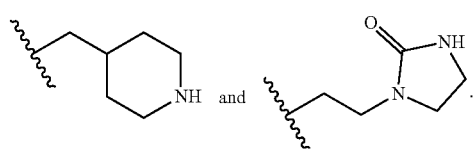 [SMILES: *CC1CCNCC1 ; "and" ; *CCN1CCNC1=O ; "."]

For the purpose of the present disclosure, the term "(heteroaryl)alkyl" as used by itself or as part of another group refers to an alkyl group substituted with one, two, or three optionally substituted heteroaryl groups. In one embodiment, the (heteroaryl)alkyl group is a $(C_{1-4})$alkyl substituted with one optionally substituted heteroaryl group. Non-limiting exemplary (heteroaryl)alkyl groups include:

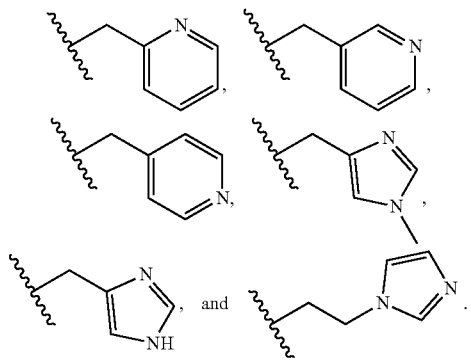

The present disclosure encompasses any of the compounds disclosed herein which are isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively, e.g., $^3H$, $^{11}C$, and $^{14}C$. Isotopically-labeled compounds can be prepared by methods known in the art.

Some of the compounds disclosed herein may contain one or more asymmetric centers and may thus give rise to enantiomers, diastereomers, and other stereoisomeric forms. The present disclosure is meant to encompass the use of all such possible forms, as well as their racemic and resolved forms and mixtures thereof. The individual enantiomers can be separated according to methods known in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present disclosure as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The term "about," as used herein in connection with a measured quantity, refers to the normal variations in that measured quantity, as expected by the skilled artisan making the measurement and exercising a level of care commensurate with the objective of measurement and the precision of the measuring equipment.

As used herein, the terms "xylene solubility" and "xylene solubles content" refer to a measurement result of the Xylene Soluble test method of ASTM D5492, and is given in units of % XS.

DETAILED DESCRIPTION

The present invention has been described with reference to specific exemplary embodiments thereof. It will, however, be evident that various modifications and changes may be made thereto without departing from the broader scope of the embodiments of the invention as set for in the appended claims. The specification and drawings are, accordingly, to be regarded in an illustrative rather than a restrictive sense.

Certain embodiments of the present invention are directed to a compound of Formula I:

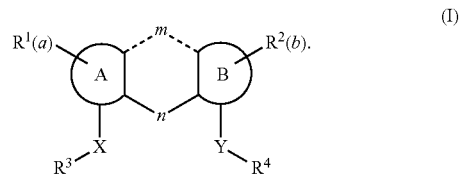

In one embodiment, A and B are each independently selected from a group consisting of a 5-membered aromatic, a 5-membered heteroaromatic, a 6-membered aromatic, and a 6-membered heteroaromatic.

In one embodiment, the dashed lines together (illustrated above as connecting m to A and B) are either present or non-existent with the proviso that m is non-existent when the dashed lines are non-existent. In such embodiments where the dashed lines are non-existent, A and B are bridged by n alone.

In one embodiment, m and n are each independently non-existent, optionally substituted alkylene, optionally substituted alkenylene, or optionally substituted alkynylene. In one embodiment, A, B, m, and n together form a bridged aromatic system, with the proviso that the dashed lines are present. It is to be understood that m and n may form single or double bonds with to A and B, and may form resonance structures with A and B.

In one embodiment, a and b are each independently selected from a group consisting of 0, 1, 2, and 3.

In one embodiment, X and Y are each independently a moiety selected from a group consisting of —C—O—, —O—, —S—, —SO—, —SO$_2$—, —OS(=O)$_2$O—, —OS(=O)O—, —S(=O)O—, —(CR$^{5a}$R$^{5b}$)—, —NR$^6$—, —SO$_2$NR$^7$—, —NR$^7$SO$_2$—, —OP(=O)(OR$^8$)O—, —OP(=O)(H)O—, —OP(OH)O—, —(C=O)—O—, —O—(C=O)—, —(C=O)—, —Si(=O)—, —Si(R$^8$)$_2$—, —Ge(=O)—, and —Ge(R$^8$)$_2$—.

In one embodiment, each occurrence of R$^1$ and R$^2$ is independently selected from the group consisting of halogen, hydroxy, optionally substituted alkyl, optionally substituted alkoxy, optionally substituted alkenyl, optionally substituted alkynyl, aralkyl, (heterocyclo)alkyl, (heteroaryl)alkyl, (amino)alkyl, (alkylamino)alkyl, (dialkylamino)alkyl, (carboxamido)alkyl, (cyano)alkyl, alkoxyalkyl, hydroxyalkyl, heteroalkyl, optionally substituted cycloalkyl, optionally substituted cycloalkoxy, optionally substituted aryl, optionally substituted heterocyclo, and optionally substituted heteroaryl; or any two adjacent occurrences of $R^1$ and $R^2$ together with the atom to which they are attached form a 3- to 8-membered optionally substituted cycloalkyl, a 3- to 8-membered heterocyclo, a 3- to 8-membered optionally substituted aromatic, or a 3- to 8-membered heteroaromatic.

In one embodiment, $R^3$ and $R^4$ are each independently selected from the group consisting of hydrogen, halogen, hydroxy, optionally substituted alkyl, optionally substituted alkenyl, cycloalkenyl, optionally substituted cycloalkenyl, optionally substituted alkynyl, aralkyl, (heterocyclo)alkyl, (heteroaryl)alkyl, (amino)alkyl, (alkylamino)alkyl, (dialkylamino)alkyl, (carboxamido)alkyl, (cyano)alkyl, alkoxyalkyl, hydroxyalkyl, heteroalkyl, optionally substituted cycloalkyl, optionally substituted aryl, optionally substituted heterocyclo, and optionally substituted heteroaryl.

In one embodiment, $R^{5a}$ and $R^{5b}$ are each independently selected from a group consisting of hydrogen, halogen, and alkyl.

In one embodiment, $R^6$ and $R^7$ are each independently selected from a group consisting of hydrogen and alkyl.

In one embodiment, $R^8$ is selected from a group consisting of hydrogen, halogen, alkyl, alkenyl, alkynyl, aryl, carbonyl, alkoxyl, and optionally substituted forms thereof.

Certain other embodiments of the present invention are directed to a compound of Formula I. In one embodiment, m is non-existent. In another embodiment, n is non-existent. In yet another embodiment, both m and n are non-existent. In yet another embodiment, A is 6-membered aromatic. In one embodiment, B is 6-membered aromatic. In one embodiment, both A and B are 6-membered aromatic. In one embodiment, a is 0. In one embodiment, b is 0. In one embodiment, both a and b are 0. In one embodiment, X is —(C=O)—O—. In one embodiment, Y is —(C=O)—O—. In one embodiment, both X and Y are —(C=O)—O—. In one embodiment, $R^3$ is optionally substituted alkyl. In one embodiment, $R^4$ is optionally substituted alkyl. In one embodiment, both $R^3$ and $R^4$ are optionally substituted alkyl. In one embodiment, $R^3$ is butyl. In one embodiment, $R^4$ is butyl. In one embodiment, both $R^3$ and $R^4$ are butyl. In one embodiment, m or n is non-existent, A or B is 6-membered aromatic, a or b is 0, X or Y is —(C=O)—O—, and $R^3$ or $R^4$ is optionally substituted alkyl or butyl.

Certain other embodiments of the present invention are directed to a compound of Formula II:

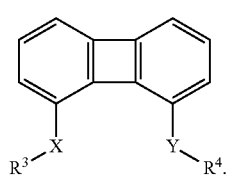

(II)

Certain other embodiments of the present invention are directed to a compound of Formula III:

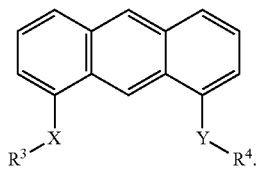

(III)

Certain other embodiments of the present invention are directed to a compound of Formula IV:

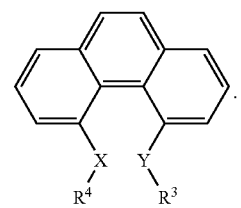

(IV)

Certain other embodiments of the present invention are directed to a compound of Formula V:

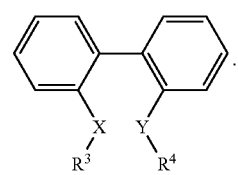

(V)

In certain embodiments, A and B are 6-membered aromatic, and m and n are both non-existent (i.e., a A and B are bonded directly together in place of m and n, for example, as shown in Formula II), are both —CH— (e.g., as shown in Formula III), or n is non-existent and m is —(CH)$_2$— (e.g., as shown in Formula IV). In certain embodiments, A and B are 6-membered aromatic, m and n are both non-existent and the dashed lines of Formula I are non-existent (e.g., as shown in Formula V).

In certain embodiments, X and Y are each independently a moiety selected from the group consisting of —C—O, —O—, —(CR$^{5a}$R$^{5b}$)—, —(C=O)—O—, —O—(C=O)—, and —(C=O)—. In certain embodiments, X and Y are each independently a moiety selected from the group consisting of —C—O—, —(C=O)—O—, —O—(C=O)—, and —(C=O)—. In certain embodiments, X and Y are each independently a moiety selected from the group consisting of —C—O—, —O—, —SO—, —SO$_2$—, —OS(=O)$_2$O—, —OS(=O)O—, —S(=O)O—, —(CR$^{5a}$R$^{5b}$)—, —(C=O)—O—, —O—(C=O)—, and —(C=O)—. In certain embodiments, X and Y are each independently a moiety selected from the group consisting of —C—O—, —O—, —(CR$^{5a}$R$^{5b}$)—, —NR$^6$—, —NR$^7$SO$_2$—, —(C=O)—O—, —O—(C=O)—, and —(C=O)—. In certain embodiments, X and Y are each independently a moiety selected from the group consisting of —C—O—, —O—, —OP(=O)(OR$^8$)O—, —OP(=O)(H)O—, —OP(OH)O—, —(C=O)—O—, —O—

(C=O)—, and —(C=O)—. In certain embodiments, X and Y are each independently a moiety selected from the group consisting of —C—O—, —O—, —(C=O)—O—, —O—(C=O)—, —(C=O)—, —Si(=O)—, —Si($R^8$)$_2$—, —Ge(=O)—, and —Ge($R^8$)$_2$—.

In certain embodiments, each occurrence of $R^1$ and $R^2$ is independently selected from the group consisting of halogen, hydroxy, optionally substituted alkyl, optionally substituted alkoxy, optionally substituted alkenyl, optionally substituted alkynyl, aralkyl, (heterocyclo)alkyl, (heteroaryl)alkyl, (amino)alkyl, (alkylamino)alkyl, (dialkylamino)alkyl, (carboxamido)alkyl, (cyano)alkyl, alkoxyalkyl, hydroxyalkyl, heteroalkyl, optionally substituted cycloalkyl, optionally substituted cycloalkoxy, optionally substituted aryl, optionally substituted heterocyclo, and optionally substituted heteroaryl. In certain embodiments, each occurrence of $R^1$ and $R^2$ is independently selected from the group consisting of halogen, hydroxy, optionally substituted alkyl, optionally substituted alkoxy, optionally substituted alkenyl, optionally substituted alkynyl, and aralkyl. In certain embodiments, each occurrence of $R^1$ and $R^2$ is independently selected from the group consisting of (heterocyclo)alkyl, (heteroaryl)alkyl, (amino)alkyl, (alkylamino)alkyl, (dialkylamino)alkyl, (carboxamido)alkyl, (cyano)alkyl, alkoxyalkyl, hydroxyalkyl, heteroalkyl, optionally substituted cycloalkyl, optionally substituted cycloalkoxy, optionally substituted aryl, optionally substituted heterocyclo, and optionally substituted heteroaryl. In certain embodiments, any two adjacent occurrences of $R^1$ and $R^2$ together with the atom to which they are attached form a 3- to 8-membered optionally substituted cycloalkyl, a 3- to 8-membered heterocyclo, a 3- to 8-membered optionally substituted aromatic, or a 3- to 8-membered heteroaromatic.

In certain embodiments, $R^3$ and $R^4$ are each independently selected from the group consisting of hydrogen, halogen, hydroxy, optionally substituted alkyl, optionally substituted alkenyl, cycloalkenyl, optionally substituted cycloalkenyl, optionally substituted alkynyl, aralkyl, (heterocyclo)alkyl, (heteroaryl)alkyl, (amino)alkyl, (alkylamino)alkyl, (dialkylamino)alkyl, (carboxamido)alkyl, (cyano)alkyl, alkoxyalkyl, hydroxyalkyl, heteroalkyl, optionally substituted cycloalkyl, optionally substituted aryl, optionally substituted heterocyclo, and optionally substituted heteroaryl.

In certain embodiments, $R^3$ and $R^4$ are each independently selected from the group consisting of hydrogen, halogen, and hydroxyl. In certain embodiments, $R^3$ and $R^4$ are each independently selected from the group consisting of optionally substituted alkyl, optionally substituted alkenyl, cycloalkenyl, optionally substituted cycloalkenyl, optionally substituted alkynyl, aralkyl, (heterocyclo)alkyl, (heteroaryl)alkyl, (amino)alkyl, (alkylamino)alkyl, (dialkylamino)alkyl, (carboxamido)alkyl, (cyano)alkyl, alkoxyalkyl, hydroxyalkyl, and heteroalkyl. In certain embodiments, $R^3$ and $R^4$ are each independently selected from the group consisting of optionally substituted cycloalkyl, optionally substituted aryl, optionally substituted heterocyclo, and optionally substituted heteroaryl.

In certain embodiments, $R^3$ and $R^4$ are each independently selected from the group consisting of hydrogen, halogen, hydroxyl, optionally substituted alkyl, optionally substituted alkenyl, cycloalkenyl, optionally substituted cycloalkenyl, optionally substituted alkynyl, aralkyl, (heterocyclo)alkyl, (heteroaryl)alkyl, (amino)alkyl, (alkylamino)alkyl, (dialkylamino)alkyl, (carboxamido)alkyl, (cyano)alkyl, alkoxyalkyl, hydroxyalkyl, and heteroalkyl. In certain embodiments, $R^3$ and $R^4$ are each independently selected from the group consisting of hydrogen, halogen, hydroxyl, optionally substituted cycloalkyl, optionally substituted aryl, optionally substituted heterocyclo, and optionally substituted heteroaryl.

In one embodiment, $R^8$ is selected from a group consisting of alkyl, alkenyl, alkynyl, aryl, carbonyl, alkoxyl, and optionally substituted forms thereof.

It is to be understood that various combinations and subcombinations of the aforementioned variables and moieties are contemplated.

In certain embodiments, a polyolefin catalyst includes a solid catalyst component comprising an aluminum alkyl, a metal component, and an electron donor. In one embodiment, the electron donor is a compound having a form of any of Formulas I, II, III, IV, or V. In one embodiment, the metal component is titanium. In other embodiments, other suitable metals may be used. In one embodiment, the polyolefin catalyst further includes a support. The metal component and the electron donor may form a catalyst disposed on the support (e.g., a $MgCl_2$ support). In one embodiment, the support includes magnesium (e.g., in a form of an oxide). In certain embodiments, the aluminum alkyl comprises trietylaluminium (TEAL).

In one embodiment, the polyolefin catalyst has an activity of greater than 20 kg/g·hr. In one embodiment, the polyolefin catalyst has an activity of greater than 10 kg/g·hr. In one embodiment, the polyolefin catalyst has an activity of greater than 20 kg/g·hr. In one embodiment, the polyolefin catalyst has an activity of greater than 30 kg/g·hr. In one embodiment, the polyolefin catalyst has an activity of greater than 35 kg/g·hr.

In one embodiment, the polyolefin catalyst is adapted to produce polypropylene having a polydispersity index (PI) of greater than 2. In one embodiment, the polyolefin catalyst is adapted to produce polypropylene having a PI of greater than 2.5. In one embodiment, the polyolefin catalyst is adapted to produce polypropylene having a PI of greater than 3.

In one embodiment, the polyolefin catalyst is adapted to produce polypropylene having a xylene solubles content of less than 4% XS. In one embodiment, the polyolefin catalyst is adapted to produce polypropylene having a xylene solubles content of less than 6% XS. In one embodiment, the polyolefin catalyst is adapted to produce polypropylene having a xylene solubles content of less than 8% XS.

In one embodiment, the polyolefin catalyst is adapted to produce polypropylene having a melt flow index of greater than 0.5 g/10 min. In one embodiment, the polyolefin catalyst is adapted to produce polypropylene having a melt flow index of greater than 2 g/10 min. In one embodiment, the polyolefin catalyst is adapted to produce polypropylene having a melt flow index of greater than 5 g/10 min.

In one embodiment, a method for producing a polyolefin catalyst includes forming a reaction mixture that includes a support and a titanium salt, and adding an electron donor to the reaction mixture to form the polyolefin catalyst. In some embodiments, the electron donor is a compound having a form of any of Formulas I, II, III, IV, or V. The resulting polyolefin catalyst, in some embodiments, has an activity of greater than 10 kg/g·hr, greater than 20 kg/g·hr, greater than 30 kg/g·hr, or greater than 35 kg/g·hr. In one embodiment, the support includes magnesium. In one embodiment, the support includes a magnesium halide. In one embodiment, the resulting polyolefin catalyst is adapted to produce polypropylene having a polydispersity index (PI) of greater than 3. The resulting polyolefin catalyst, in some embodiments, is adapted to produce polypropylene having a xylene solubles content of less than 4% XS, less than 6% XS, or less than 8%

XS. The resulting polyolefin catalyst, in some embodiments, is adapted to produce polypropylene having a melt flow index of greater than 0.5 g/10 min, greater than 2 g/10 min, or greater than 5 g/10 min.

In one embodiment, a method for producing polypropylene includes forming a reaction mixture by mixing a silane component with a catalyst component, with the catalyst component including a titanium catalyst and an electron donor (e.g., a compound having a form of any of Formulas I, II, III, IV, or V). The method further includes adding propylene to the reaction mixture to form a polypropylene batch, wherein a polydispersity index (PI) of the polypropylene batch is greater than 3, wherein a xylene solubles content of the polypropylene batch is less than 3% XS, and wherein a melt flow index of the polypropylene is greater than 5 g/10 min. In one embodiment, the catalyst component is in a form of a slurry.

In one embodiment, a catalyst system (e.g., for use in olefinic polymerization) includes an organoaluminum compound, an organosilicon compound, and a compound having a form of any of Formulas I, II, III, IV, or V. In one embodiment, the organosilicon compound is of a form of $R^9_k Si(OR^{10})_{4-k}$, wherein $R^9$ and $R^{10}$ are each hydrocarbon, and wherein k is 0, 1, 2, or 3. In one embodiment, the organosilicon compound is of a form of $SiR^9R^{10}_k(OR^{11})_{3-k}$, wherein $R^9$ is cyclic hydrocarbon or substituted cyclic hydrocarbon, wherein $R^{10}$ and $R^{11}$ are each hydrocarbon, and wherein k is 0, 1, or 2.

In one embodiment, a method of polymerizing or copolymerizing an olefin monomer includes polymerizing or copolymerizing the olefin monomer in the presence of any of the catalyst systems described herein to form a polymer or copolymer, respectively. The method further includes recovering the polymer or copolymer. In one embodiment, the olefin monomer is ethylene, propylene, 1-butylene, 4-methyl-1-pentene, 1-hexane, 1-octene, or a combination thereof, with homopolymers and copolymers thereof being contemplated.

ILLUSTRATIVE EXAMPLES

The following illustrative examples provide experimental conditions for producing and utilizing catalysts in accordance with some of the embodiments described herein. The examples set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

Example 1: Internal Electron Donor Examples

Compounds of Formulas II.a, III.a, III.b, IV.a, IV.b, IV.c, and V.a were used as internal electron donors in the Examples that follow:

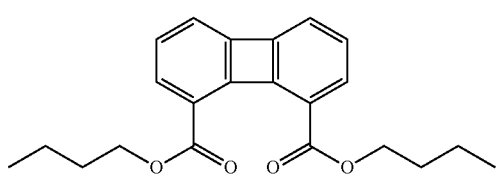
(II.a)

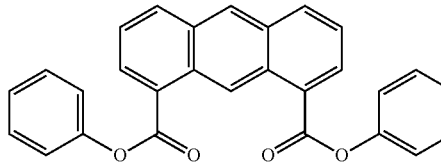
(III.a)

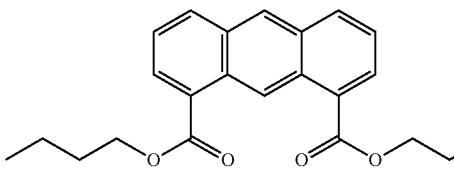
(III.b)

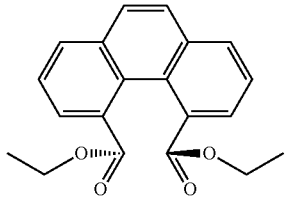
(IV.a)

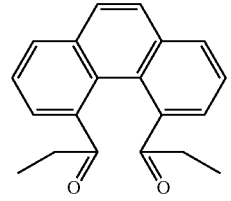
(IV.b)

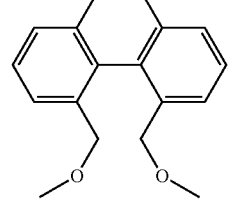
(IV.c)

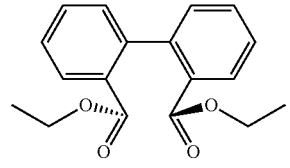
(V.a)

Example 2: Catalyst Preparation

A reaction mixture was prepared by adding 3.3 g $MgCl_2$, 0.8 g phthalic anhydride, 6.41 g epichlorohydrin, 6.70 g tributylphosphate, and 40.92 g toluene into a 250 mL reactor under nitrogen. The reaction mixture was heated to 60° C. and agitated at 400 rpm for 2 hours. The reaction mixture was subsequently cooled to −30° C., followed by the addition of 65 g $TiCl_4$ with the reactor being maintained at −25° C. during the addition. The agitation was reduced to 200 rpm and the reactor was heated to 85° C. in two hours. The agitation was then increased to 400 rpm for 30 minutes, and 3.9 mmol of the compound of Formula II.a was added to the reaction mixture, stirred for one hour, and filtered. 38 mL toluene and an additional 2.08 mmol of the compound of Formula II.a were added into the reactor mixture, and the reaction mixture was heated to 85° C. at 400 rpm, stirred for one hour, and filtered. The heat was then turned off, and the reaction mixture was washed with 65 mL toluene and filtered. An additional 65 mL toluene was added, and the reaction mixture was maintained under nitrogen overnight without stirring. The toluene was removed by filtering, and 66.25 mL of 10 wt % $TiCl_4$-toluene was added. The reaction mixture was heated to 95° C. at 400 rpm for one hour and filtered. The previous step was repeated 3 times at 110° C., 400 rpm, and 30 minutes each. The resulting catalyst was washed 4 times with 65 mL hexane and collected as a hexane slurry.

Example 3: Polymerization Procedure Using Formula II.a Compound

Propylene polymerization was performed in a one gallon reactor. The reactor was purged at 100° C. under nitrogen for one hour. At room temperature, 1.5 mL of 25 wt % triethylaluminum in heptane was added into the reactor, followed by 0.94 mL of 0.0768 M cyclohexylmethyl dimethoxysilane, and followed by 7.0 mg of the catalyst of Example 2 as a 1 wt % hexane slurry. The reactor was charged with 4 standard liters (SL) $H_2$, followed by 1300 g propylene. The reactor was heated to and held at 70° C. for one hour, followed by venting of the reactor and recovery of the polymer (polypropylene). The overall activity of the catalyst was 30.8 kg/g·hr. The xylene solubles content of the resulting polypropylene was 3.09% XS. The melt flow index of the resulting polypropylene was 7 g/10 min. The polydispersity index of the resulting polypropylene was 3.83.

In another batch prepared with the compound of Formula II.a as an internal donor under similar conditions, an overall activity of the catalyst was 30.7 kg/g·hr. The xylene solubles content of the resulting polypropylene was 2.75% XS. The melt flow index of the resulting polypropylene was 8.7 g/10 min. The polydispersity index of the resulting polypropylene was 4.23.

Propylene polymerization was again performed in a similar fashion as described in above, except that the reactor was charged with 40 standard liters $H_2$ rather than 4 standard liters $H_2$. An overall activity of the catalyst was 33.6 kg/g·hr. The xylene solubles content of the resulting polypropylene was 4.09% XS. The melt flow index of the resulting polypropylene was 261 g/10 min. In another batch prepared under similar conditions, an overall activity of the catalyst was 37.4 kg/g·hr. The xylene solubles content of the resulting polypropylene was 4.12% XS. The melt flow index of the resulting polypropylene was 205 g/10 min.

Example 4: Polymerization Procedure Using Formula III.a Compound

In another batch prepared with the compound of Formula III.a as an internal donor under similar conditions described above with respect to Example 2, an overall activity of the catalyst was 14.3 kg/g·hr. The xylene solubles content of the resulting polypropylene was 8.2% XS. The melt flow index of the resulting polypropylene was too high to be measured.

Example 5: Polymerization Procedure Using Formula III.b Compound

In another batch prepared with the compound of Formula III.b as an internal donor under similar conditions, an overall activity of the catalyst was 16.3 kg/g·hr. Xylene solubles content and melt flow index were not acquired.

Example 6: Polymerization Procedure Using Formula IV.a Compound

In another batch prepared with the compound of Formula IV.a as an internal donor under similar conditions described above with respect to Example 2, an overall activity of the catalyst was 5.1 kg/g·hr. Xylene solubles content and melt flow index were not acquired.

Example 7: Polymerization Procedure Using Formula IV.b Compound

In another batch prepared with the compound of Formula IV.b as an internal donor under similar conditions described above with respect to Example 2, an overall activity of the catalyst was 12.4 kg/g·hr. Xylene solubles content and melt flow index were not acquired.

Example 8: Polymerization Procedure Using Formula IV.c Compound

In another batch prepared with the compound of Formula IV.c as an internal donor under similar conditions described above with respect to Example 2, an overall activity of the catalyst was 17.1 kg/g·hr. The xylene solubles content of the resulting polypropylene was 6.3% XS. The melt flow index of the resulting polypropylene was 10.2 g/10 min.

Example 9: Polymerization Procedure Using Formula V.a Compound

In another batch prepared with the compound of Formula V.a as an internal donor under similar conditions described above with respect to Example 2, an overall activity of the catalyst was 22.0 kg/g·hr. The xylene solubles content of the resulting polypropylene was 5.2% XS. The melt flow index of the resulting polypropylene was 5.3 g/10 min. The polydispersity index of the resulting polypropylene was not measured.

The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Reference throughout this specification to "an embodiment" or "one embodiment" means that a particular feature, structure, or characteristic described in connection with the embodiment is included in at least one embodiment. Thus, the appearances of the phrase "an embodiment" or "one embodiment" in various places throughout this specification are not necessarily all referring to the same embodiment.

It is to be understood that the above description is intended to be illustrative, and not restrictive. Many other embodiments will be apparent to those of skill in the art upon reading and understanding the above description. The scope of the disclosure should, therefore, be determined with reference to the appended claims, along with the full scope of equivalents to which such claims are entitled.

What is claimed is:

1. A polyolefin catalyst comprising an aluminum alkyl, a metal component, and an electron donor of Formula II.a, III.a., III.b., IV.a., or IV.b.:

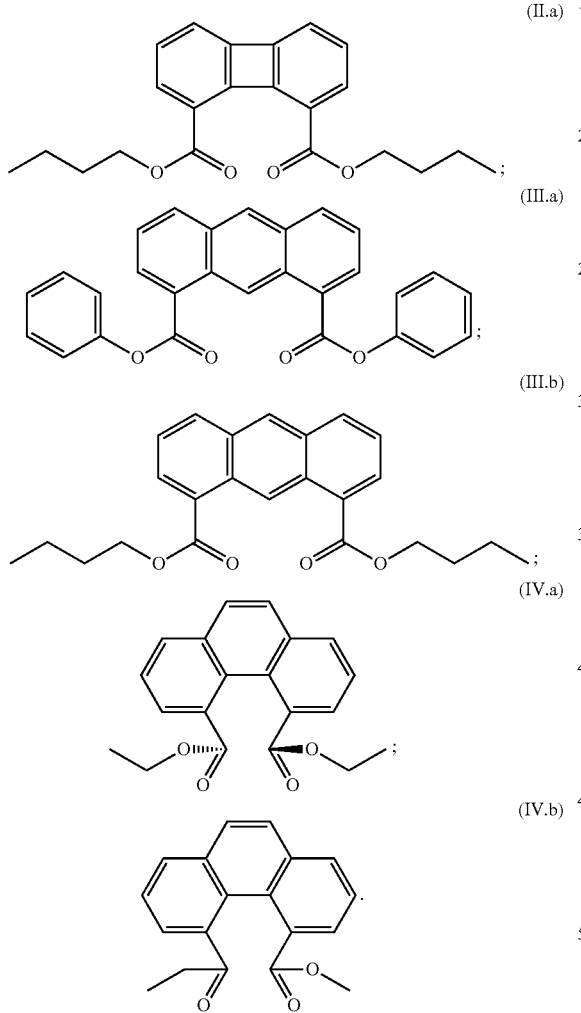

2. The polyolefin catalyst of claim 1, wherein the metal component is titanium.
3. The polyolefin catalyst of claim 1, further comprising a support, wherein the metal component and the electron donor form a catalyst disposed on the support.
4. The polyolefin catalyst of claim 3, wherein the support comprises a magnesium halide.
5. The polyolefin catalyst of claim 1, wherein the polyolefin catalyst has an activity of greater than 25 kg/g·hr.
6. The polyolefin catalyst of claim 1, wherein the polyolefin catalyst has an activity of greater than 30 kg/g·hr.

7. The polyolefin catalyst of claim 1, wherein the polyolefin catalyst is adapted to produce polypropylene having a polydispersity index (PI) of greater than 3.
8. The polyolefin catalyst of claim 1, wherein the polyolefin catalyst is adapted to produce polypropylene having a xylene solubles content of less than 8% XS.
9. The polyolefin catalyst of claim 1, wherein the polyolefin catalyst is adapted to produce polypropylene having a melt flow index of greater than 2 g/10 min.
10. A method for producing polypropylene, the method comprising:
    forming a reaction mixture by mixing a silane component with a catalyst, the catalyst component comprising a titanium catalyst, an electron donor, and a magnesium halide; and
    adding propylene to the reaction mixture to form a polypropylene batch, wherein a polydispersity index (PI) of the polypropylene batch is greater than 3, wherein a xylene solubles content of the polypropylene batch is less than 8% XS, and wherein a melt flow index of the polypropylene is greater than 2 g/10 min;
    wherein the electron donor is of Formula II.a, III.a., III.b., IV.a., or IV.b.:

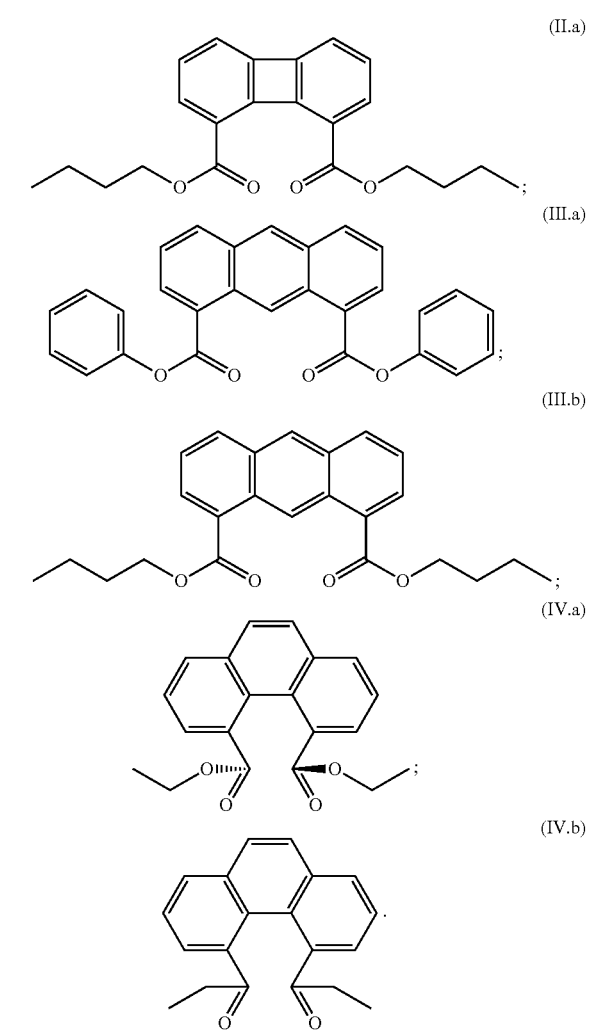

* * * * *